United States Patent
Baldovino et al.

(10) Patent No.: US 10,549,723 B2
(45) Date of Patent: Feb. 4, 2020

(54) VEHICLE OBJECT-DETECTION SENSOR ASSEMBLY

(71) Applicant: Ford Global Technologies, LLC, Dearborn, MI (US)

(72) Inventors: Segundo Baldovino, Novi, MI (US); Haiping Hong, Canton, MI (US); Venkatesh Krishnan, Canton, MI (US); Andre Sykula, Sterling Heights, MI (US); Sunil Patil, Troy, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 15/971,018

(22) Filed: May 4, 2018

(65) Prior Publication Data

US 2019/0337489 A1    Nov. 7, 2019

(51) Int. Cl.
*B60S 1/02* (2006.01)
*B60S 1/48* (2006.01)
*G01N 21/958* (2006.01)
*B60S 1/54* (2006.01)

(52) U.S. Cl.
CPC ............ *B60S 1/481* (2013.01); *B60S 1/548* (2013.01); *G01N 21/958* (2013.01); *G01N 2021/9586* (2013.01)

(58) Field of Classification Search
None
See application file for complete search history.

(56) References Cited

U.S. PATENT DOCUMENTS

| | | | |
|---|---|---|---|
| 6,554,210 B2 | 4/2003 | Holt et al. | |
| 6,607,606 B2* | 8/2003 | Bronson | B08B 17/02 134/104.1 |
| 7,506,823 B2* | 3/2009 | Eisele | B05B 1/12 239/284.1 |
| 9,180,840 B2* | 11/2015 | Tanaka | B60S 1/56 |
| 9,467,687 B2* | 10/2016 | Takemura | H04N 17/002 |
| 9,505,382 B2 | 11/2016 | Gokan | |
| 9,539,988 B2* | 1/2017 | Hsiao | B08B 3/10 |
| 9,663,073 B2* | 5/2017 | Tanaka | B60S 1/56 |
| 9,746,666 B2* | 8/2017 | Eineren | G03B 17/02 |
| 9,910,272 B2* | 3/2018 | Witte | B08B 3/04 |
| 10,011,251 B2* | 7/2018 | Gokan | B60S 1/50 |
| 10,095,934 B2* | 10/2018 | Takemura | G06K 9/00791 |
| 10,173,646 B1* | 1/2019 | Rice | B60S 1/56 |
| 10,183,653 B2* | 1/2019 | Davies | B60S 1/56 |
| 10,189,429 B2* | 1/2019 | Krishnan | B60R 21/01526 |
| 10,189,450 B2* | 1/2019 | Rice | B60S 1/56 |

(Continued)

FOREIGN PATENT DOCUMENTS

DE    102015210469 A1    12/2016
WO    2017169140 A1    10/2017

*Primary Examiner* — Jonathan M Dager
(74) *Attorney, Agent, or Firm* — Frank A. MacKenzie; Bejin Bieneman LLC

(57) ABSTRACT

A computer includes a processor and a memory storing processor-executable instructions. The processor is programmed to receive data indicating a contaminant on a sensor window of a vehicle; determine a combination of an air pressure setting of an air source and a liquid pressure setting of a liquid source to remove the contaminant from the sensor window; and set the air source to the air pressure setting and the liquid source to the liquid pressure setting.

18 Claims, 10 Drawing Sheets

(56) References Cited

U.S. PATENT DOCUMENTS

| | | | |
|---|---|---|---|
| 10,220,817 B2* | 3/2019 | Rice | B60S 1/56 |
| 10,252,703 B2* | 4/2019 | Ina | B60S 1/522 |
| 10,286,880 B2* | 5/2019 | Schmidt | B08B 3/02 |
| 10,409,055 B2* | 9/2019 | Leonelli, Jr. | B60S 1/482 |
| 10,421,439 B2* | 9/2019 | Hansen | B60S 1/481 |
| 2002/0005440 A1* | 1/2002 | Holt | B05B 7/08 239/284.2 |
| 2003/0155001 A1* | 8/2003 | Hoetzer | B60S 1/0822 134/37 |
| 2005/0086758 A1* | 4/2005 | Arkashevski | B60S 1/32 15/250.02 |
| 2006/0086827 A1 | 4/2006 | Sekiya | |
| 2009/0250533 A1* | 10/2009 | Akiyama | B60S 1/381 239/284.1 |
| 2011/0292212 A1* | 12/2011 | Tanabe | B05B 1/08 348/148 |
| 2012/0117745 A1* | 5/2012 | Hattori | B60S 1/0848 15/250.01 |
| 2013/0092758 A1* | 4/2013 | Tanaka | B60S 1/52 239/284.1 |
| 2014/0009615 A1* | 1/2014 | Kiyohara | H04N 7/18 348/148 |
| 2014/0010408 A1* | 1/2014 | Irie | G06K 9/00791 382/103 |
| 2014/0060582 A1* | 3/2014 | Hartranft | B60R 11/04 134/18 |
| 2014/0232869 A1* | 8/2014 | May | H04N 7/18 348/148 |
| 2014/0270379 A1* | 9/2014 | Snider | B60R 1/00 382/104 |
| 2015/0040953 A1* | 2/2015 | Kikuta | B60S 1/52 134/123 |
| 2015/0066293 A1* | 3/2015 | Davies | B60S 1/0862 701/36 |
| 2015/0078940 A1* | 3/2015 | Kikuta | F04B 13/02 417/432 |
| 2015/0090291 A1* | 4/2015 | Na | B60S 1/56 134/6 |
| 2015/0138357 A1* | 5/2015 | Romack | H04N 7/185 348/148 |
| 2015/0151722 A1* | 6/2015 | Gokan | B60S 1/50 134/102.2 |
| 2015/0172582 A1* | 6/2015 | Kiyohara | G06K 9/00791 348/322 |
| 2015/0177512 A1* | 6/2015 | Hayakawa | B60S 1/56 348/148 |
| 2015/0203076 A1* | 7/2015 | Irie | H04N 5/2171 134/56 R |
| 2015/0203077 A1* | 7/2015 | Gokan | B60S 1/0848 134/36 |
| 2015/0277111 A1* | 10/2015 | Bell | G02B 27/0006 359/509 |
| 2015/0298657 A1* | 10/2015 | Kanter | B60S 1/0848 348/148 |
| 2015/0343999 A1* | 12/2015 | Lopez Galera | B08B 3/02 134/30 |
| 2016/0001330 A1* | 1/2016 | Romack | B08B 3/02 134/18 |
| 2016/0176384 A1* | 6/2016 | Dissette | B60S 1/52 134/34 |
| 2017/0036650 A1* | 2/2017 | Hester | G02B 13/04 |
| 2017/0072909 A1* | 3/2017 | Giraud | B60S 1/524 |
| 2017/0259788 A1* | 9/2017 | Villa-Real | B60S 1/488 |
| 2017/0313286 A1* | 11/2017 | Galera | B60S 1/52 |
| 2018/0015908 A1* | 1/2018 | Rice | B60S 1/56 |
| 2018/0086316 A1* | 3/2018 | Trebouet | B05B 15/70 |
| 2018/0096474 A1* | 4/2018 | Guerreiro | G06T 7/0002 |
| 2018/0186342 A1* | 7/2018 | Kubota | H04N 5/225 |
| 2018/0194330 A1* | 7/2018 | Ichikawa | H04N 7/18 |
| 2018/0272996 A1* | 9/2018 | Nielsen | B60S 1/54 |
| 2018/0361997 A1* | 12/2018 | Schmidt | B60R 11/04 |
| 2018/0370496 A1* | 12/2018 | Sykula | B60S 1/485 |
| 2019/0015536 A1* | 1/2019 | Dellock | A61L 2/10 |
| 2019/0016307 A1* | 1/2019 | Negi | G01S 19/51 |
| 2019/0039575 A1* | 2/2019 | Hansen | B60S 1/481 |
| 2019/0047522 A1* | 2/2019 | Giraud | B60S 1/485 |
| 2019/0077318 A1* | 3/2019 | Datta Gupta | B60R 1/10 |
| 2019/0099768 A1* | 4/2019 | Romack | B60S 1/48 |
| 2019/0106085 A1* | 4/2019 | Bacchus | B60S 1/04 |
| 2019/0118776 A1* | 4/2019 | Krishnan | B60S 1/0807 |
| 2019/0168718 A1* | 6/2019 | Kiyama | B60S 1/485 |

* cited by examiner

VEHICLE OBJECT-DETECTION SENSOR ASSEMBLY

BACKGROUND

Vehicles, such as autonomous vehicles, typically include a variety of sensors. Some sensors detect internal states of the vehicle, for example, wheel speed, wheel orientation, and engine and transmission variables. Some sensors detect the location and/or orientation of the vehicle, for example, global positioning system (GPS) sensors; accelerometers such as piezo-electric or microelectromechanical systems (MEMS); gyroscopes such as rate, ring laser, or fiber-optic gyroscopes; inertial measurements units (IMU); and magnetometers. Some sensors are object-detection sensors that detect the external world, for example, radar sensors, scanning laser range finders, light detection and ranging (LIDAR) devices, and image processing sensors such as cameras. A LIDAR device detects distances to objects by emitting laser pulses and measuring the time of flight for the pulse to travel to the object and back. Some sensors are communications devices, for example, vehicle-to-infrastructure (V2I) or vehicle-to-vehicle (V2V) devices.

DETAILED DESCRIPTION

Figure 1:
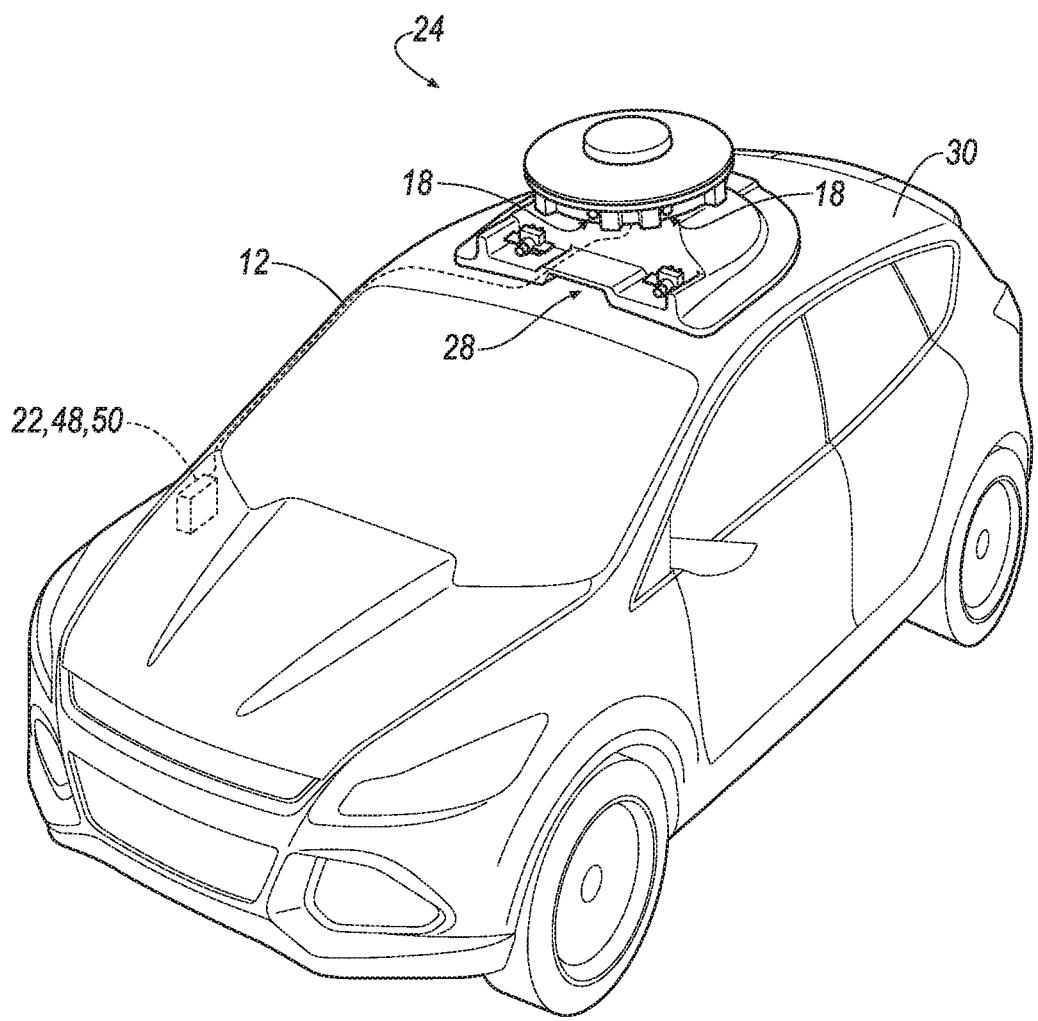
FIG. 1 is a perspective view of a vehicle with a vehicle object-detection sensor assembly.
Figure 2:
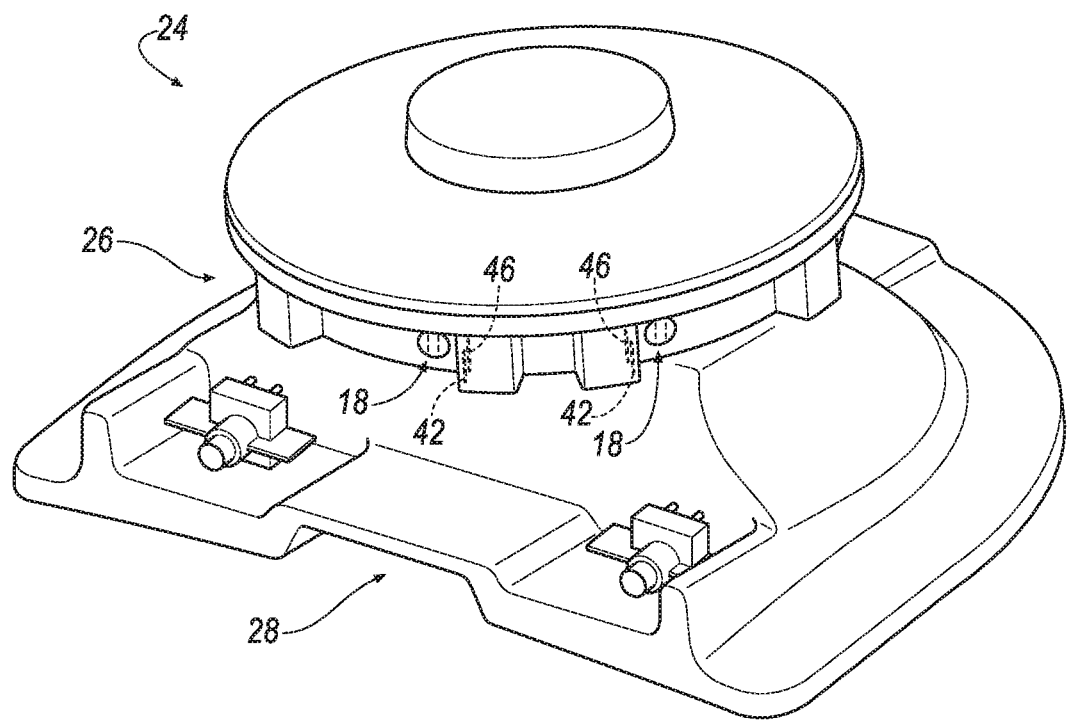
FIG. 2 is a perspective view of the vehicle object-detection sensor assembly.

With reference to the Figures, wherein like numerals indicate like parts throughout the several views, a computer 10 of a vehicle 12 includes a processor 14 and a memory 16 storing processor-executable instructions. The processor 14 is programmed to receive data indicating a contaminant on a sensor window 18 of the vehicle 12; determine a combination of an air pressure setting of an air source 20 and a liquid pressure setting of a liquid source 22 to remove the contaminant from the sensor window 18; and set the air source 20 to the air pressure setting and the liquid source 22 to the liquid pressure setting.

The air source 20 moves air across the sensor window 18, and the liquid source 22 moves liquid across the sensor window 18. The combination of the air and liquid moving across the sensor window 18 removes contaminants such as dirt, precipitation, etc., from the sensor window 18. The air pressure setting of the air source 20 and the liquid pressure setting of the liquid source 22 may be adjusted to aim the liquid at the contaminant to remove the contaminant from the sensor window 18. The computer 10 described below applies the combination of air pressure settings for the air source 20 and liquid pressure settings for the liquid source 22 to reach a desired zone 54 of sensor window 18 and remove the contaminant.

The vehicle 12 includes a sensor assembly 24 that includes a housing 26. The housing 26 may include a vent 28 to permit air intake into the housing 26. For example, the vent 28 may face in a vehicle-forward direction such that air is forced into the vent 28 during forward movement of the vehicle 12. In the example shown in the figures, the vent 28 may be partly enclosed by a roof 30 of the vehicle 12. Alternatively, the vent 28 may be defined entirely by the housing 26. In the addition, or in the alternative to facing in the vehicle-forward direction, the vent 28 may face in any suitable direction.

The housing 26 may include an air inlet 32 in fluid communication with the vent 28. The housing 26 may be shaped such that, in the example where the vent 28 faces in the vehicle-forward direction, the housing 26 directs air into the air inlet 32 as the vehicle 12 moves forward. For example, the housing 26 may enclose the vent 28 against the roof of the vehicle 12 such that, when the vehicle 12 moves forward, air is rammed through the vent 28 and into the air inlet 32. The housing 26 may include one or more air inlets 32.

The air inlet 32 may face downwardly. This configuration reduces the likelihood that falling precipitation approaches the air inlet 32.

The housing 26 may include a chamber 34 in fluid communication with the air inlet 32. In such an example, the air inlet 32 receives external air to pressurize the chamber 34.

The chamber 34 is in fluid communication with the air source 20. The air source 20 includes an air pressure source 36. The air pressure source 36 may draw air through the air inlet 32 into the chamber 34 to pressurize the chamber 34.

The sensor assembly 24 may include a membrane 38 that extends across the air inlet 32. In other words, any air that enters the chamber 34 through the air inlet 32 crosses the membrane 38. The membrane 38, for example, may allow air to flow into the air inlet 32, and may prevent other elements, e.g., water, dirt, dust, etc., from entering the air inlet 32. In an example where the housing 26 includes more than one air inlet 32, the sensor assembly 24 may include more than one membrane 38 with the membranes 38 covering the air inlets 32, respectively. The membrane 38 may include an air filter 40. The air filter 40 may be, for example, a one-way air filter, i.e., may allow air to flow into the chamber 34 through the air inlet 32, and prevent air from flowing from the chamber 34 through the air inlet 32. In the alternative, or in addition to the air filter 40, the membrane 38 may include other layers. One of the layers may include GORE-TEX®. The membrane 38 may be windproof and/or waterproof.

The housing 26 includes an air port 42. The air port 42 is in fluid communication with the chamber 34. The housing 26 may include one or more air ports 42. The housing 26 may entirely enclose the chamber 34 except for the one or more air inlets 32 and air ports 42. In other words, air may only flow through the housing 26 at the air inlets 32 and the air ports 42. As an example, air enters the chamber 34 through the air inlets 32, the air pressure source 36 pressurizes the air in the chamber 34 and the pressurized air exits the chamber 34 at the air ports 42.

The sensor assembly 24 may include one air pressure source 36 or any suitable number of air pressure sources 36. The air pressure source 36 may be a blower 44. The blower 44 may include a drive motor (not numbered) and an impeller (not numbered) rotatably coupled to the drive motor. The blower 44 may be an axial flow fan, a centrifugal fan, a cross-flow fan or any type of fan. The drive motor may be disposed above or below the impeller. The drive motor may be an electric motor having a rotational output.

The air pressure source 36 is adjustable between a plurality of air pressure settings to adjust the pressure of the air in the chamber 34. In other words, the air pressure source 36 may exert air pressure within a range, from a low air pressure to a high air pressure. The air source 20 may be adjustable between an infinite number of air pressure settings within the range, or may be adjustable between a fixed number of air pressure settings within the range. As an example, the air pressure settings may include OFF, LOW, MEDIUM and HIGH. When the air pressure setting is OFF, the air pressure source 36 is turned off. When the air pressure setting is LOW, the air pressure source 36 exerts a low air pressure. When the air pressure setting is HIGH, the air pressure source 36 exerts a high air pressure and when the air pressure is MEDIUM, the air pressure source 36 exerts a medium air pressure, midway between the low air pressure and the high air pressure. The range may include any number of settings that is suitable, e.g. the range may include multiple settings between LOW and MEDIUM and/or the range may include multiple settings between MEDIUM and HIGH. During operation of the vehicle 12, the air pressure source 36 may be powered to constantly pressurize the chamber 34 so that the air exiting the air ports 42 create air curtains across the sensor windows 18.

The housing 26 includes a liquid port 46. The liquid port 46 is in fluid communication with the liquid source 22. The housing 26 may include one or more liquid ports 46.

The liquid source 22 includes a reservoir 48 and a liquid pressure source 50. The liquid source 22 may include any suitable number of liquid pressure sources 50. The liquid pressure source 50 is in fluid communication with the reservoir 48 and is configured to move liquid from the reservoir 48 to the liquid port 46. Specifically, the liquid pressure source 50 configured to pressurize liquid from the reservoir 48, and the pressurized liquid exits the liquid port 46. The liquid source 22 may include any suitable number of tubes (not shown), channels (not shown), etc., to connect the reservoir 48, liquid pressure source 50, liquid port 46, etc. The reservoir 48 may, for example, also be connected to a windshield wiper system to supply liquid to clean a windshield of the vehicle. In such an example, the liquid may be any suitable type of windshield cleaning fluid, solvent, etc.

The liquid pressure source 50 may include a pump (not shown). The pump may be an axial pump, a triplex pump, or any suitable type of pump.

The liquid pressure source 50 is adjustable between a plurality of liquid pressure settings to adjust the pressure of the liquid supplied to the liquid port 46. The liquid source 22, e.g., the liquid pressure source 50, may be adjustable between an infinite number of liquid pressure settings within a range, or may be adjustable between a fixed number of liquid pressure settings within the range. The liquid pressure source 50 may exert pressure within a liquid pressure range, ranging from a low liquid pressure to a high liquid pressure. The liquid pressure source 50 may have a fixed number of liquid pressure settings that align with the liquid pressure range. As an example, the liquid pressure settings may include OFF, LOW, MEDIUM and HIGH. When the liquid pressure setting is OFF, the liquid source 22 is turned off. When the liquid pressure setting is LOW, the liquid source 22 exerts a low liquid pressure. When the liquid pressure setting is HIGH, the liquid source 22 exerts a high liquid pressure and when the liquid pressure setting is MEDIUM, the liquid pressure source 50 exerts a medium liquid pressure, midway between the low liquid pressure and the high liquid pressure. The liquid pressure range may include any number of settings that is suitable, e.g. the liquid pressure range may include multiple settings between LOW and MEDIUM and/or the liquid pressure range may include multiple settings between MEDIUM and HIGH. The liquid source 22 may operate to move liquid through the liquid port 46 when a contaminant is detected on the sensor window 18.

The housing 26 may include a plurality of sensor windows 18. The sensor windows 18 are spaced from each other, i.e., walls of the housing 26 separate the sensor windows 18. The sensor windows 18 may face in the same or in different directions.

Figure 3:
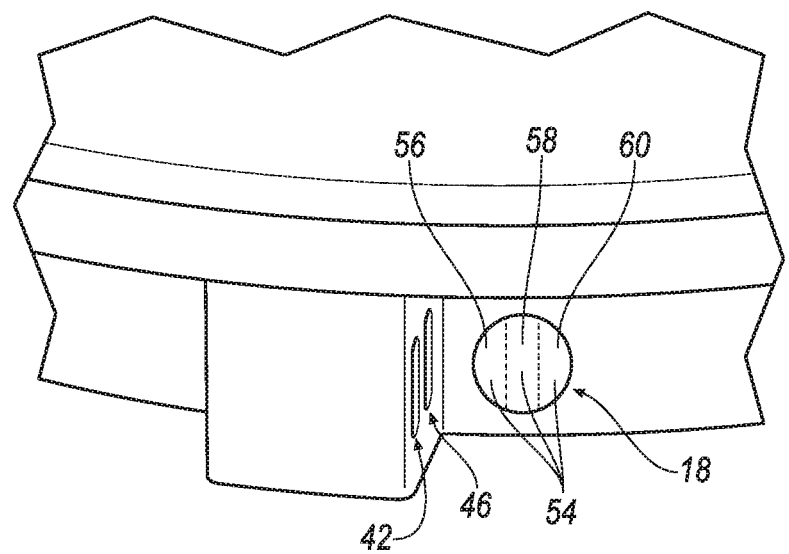
FIG. 3 is a perspective view of a portion of the vehicle object-detection sensor assembly including a sensor window divided into zones, an air port, and a liquid port.
Figure 4:
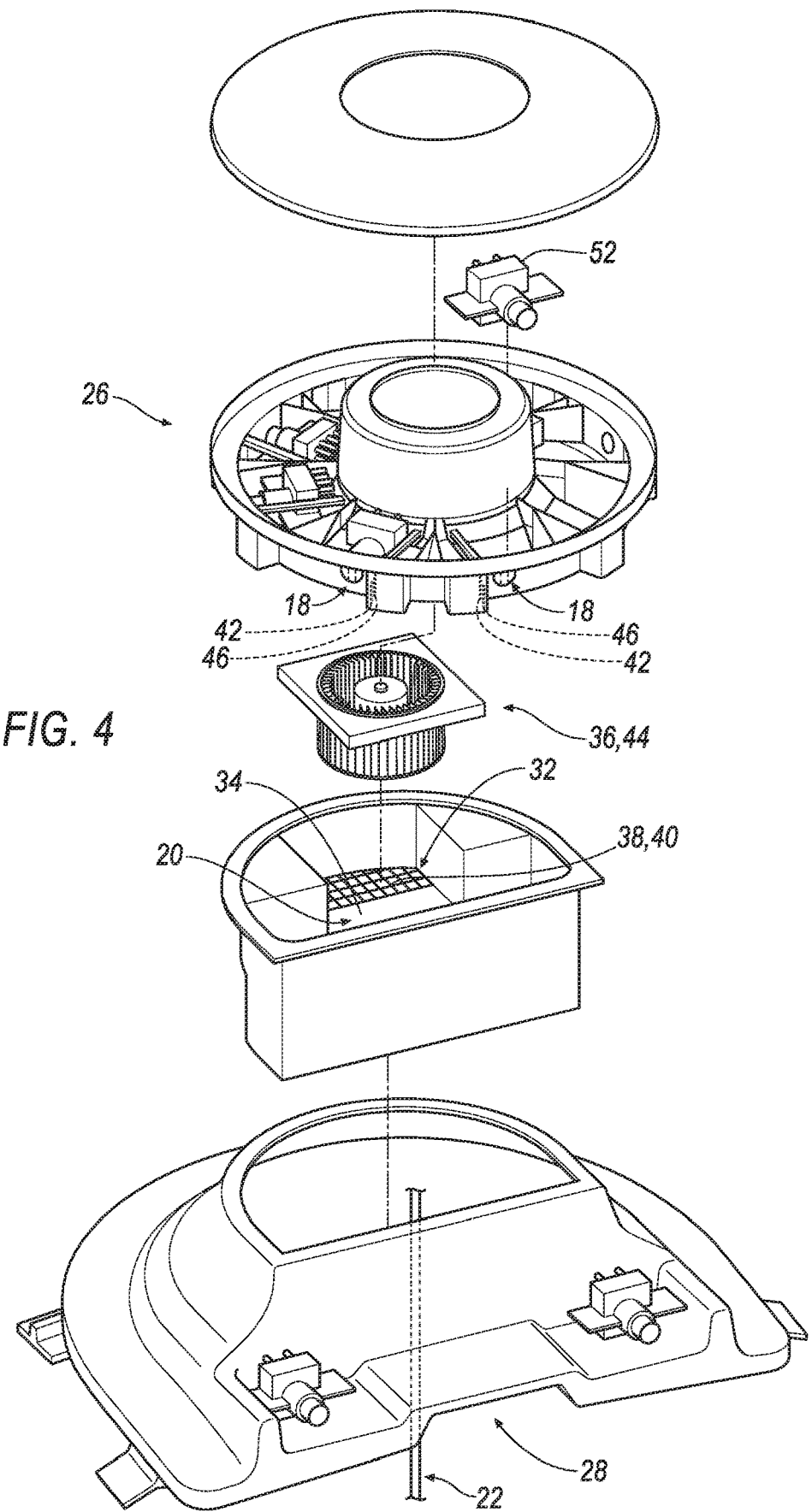
FIG. 4 is an exploded view of the vehicle object-detection sensor assembly including a pressure source, a chamber, the sensor window, the air port, and the liquid port.
Figure 5:
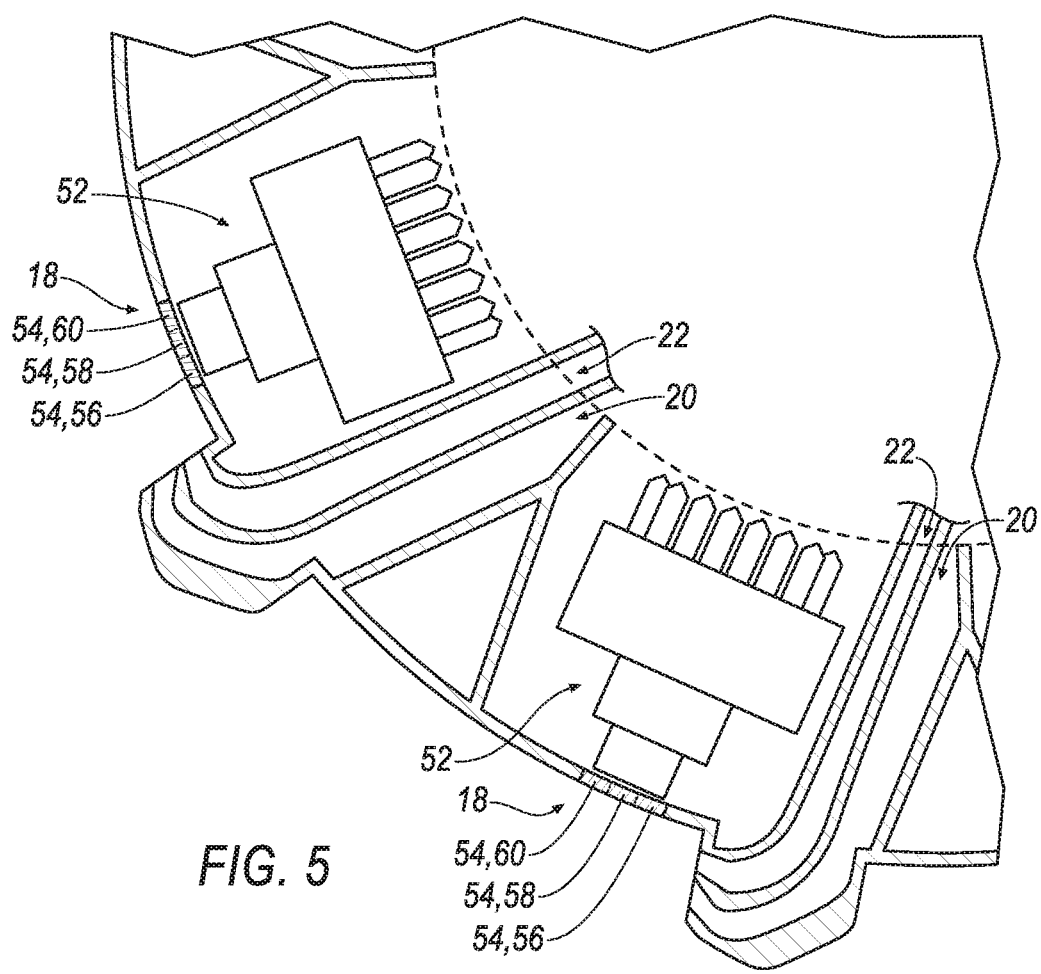
FIG. 5 is a cross-sectional view of a portion of the vehicle object-detection sensor assembly including the sensor window, the air port, and the liquid port.

Each of the sensor windows 18 may be divided into zones 54. Specifically, each of the sensor windows 18 includes a lens that may be divided into any number of zones 54 that is suitable. As an example and as shown in FIG. 3, the sensor window 18 may be divided into three zones 54. Each zone 54 may have an identifying value, and may be vertical and of equal width.

Each of the sensor windows 18 is transparent. In other words, each of the sensor windows 18 permits light to pass therethrough. Each of the sensor windows 18 may be of any suitable material, e.g., glass, plastic.

The sensor assembly 24 may include a plurality of object-detection sensors 52. At least one object-detection sensor 52 is adjacent each sensor window 18. The object-detection sensors 52 may detect the external world. For example, the object-detection sensors 52 may be radar sensors, scanning laser range finders, light detection and ranging (LIDAR) devices, image processing sensors such as cameras, or any other sensors that detect light. The object-detection sensors 52 may generate data representing an image captured by the object-detection sensors 52. Each of the object-detection sensors 52 is positioned to sense the light passing through the field of view of each of the sensor windows 18 respectively. Each of the object-detection sensors 52 can detect phenomena such as light, and sound, beginning at and outward from each related sensor window 18.

The object-detection sensor 52 may identify a location and/or a size of the contaminant on the sensor window 18 based on identifying the zone 54 through which the object-detection sensor 52 is unable to sense light. The object-detection sensor 52 may indicate that the contaminant is in the zone 54 of the sensor window 18 when the object-detection sensor 52 is unable to sense light passing through at least a part of the related zone 54. Each of the object-detection sensors 52 can detect an obstruction to the field of view of each related sensor window 18 and can generate data identifying each of the zones 54 the obstruction is in.

As set forth above, the air port 42 is in fluid communication with the chamber 34 and the liquid port 46 is in fluid communication with the reservoir 48. The housing 26 may include more than one air port 42 and/or more than one liquid port 46. In one example, as shown in FIG. 3, the air port 42 may direct air generally horizontally across the sensor window 18 and the liquid port 46 may direct liquid generally horizontally across the sensor window 18.

Each sensor window 18 is adjacent one of the air ports 42 and one of the liquid ports 46. The air port 42 and the liquid port 46 direct pressurized air and pressurized fluid respectively at the respective sensor window 18 to clean contaminants from the respective sensor window 18. As shown in FIG. 3, the air port 42 and the liquid port 46 at each sensor window 18 may be adjacent to each other. In other words, pressurized air flowing from the air port 42 flows alongside pressurized liquid from the liquid port 46, as shown in FIG. 3.

As shown in FIG. 3, the air port 42 and the liquid port 46 face the respective sensor window 18. In other words, the air port 42 and the liquid port 46 are aimed at the respective sensor window 18 so that pressurized air exiting the chamber 34 at the air port 42 and pressurized liquid exiting the reservoir 48 at the liquid port 46 flow onto the respective sensor window 18, i.e., hits directly on the respective sensor window 18.

The air ports 42 and the liquid ports 46 may have any suitable sizes and/or shapes to accomplish a desired combination of airflow and liquid flow from the air port 42 and the liquid port 46, respectively, onto the sensor window 18. As one example, the air ports 42 may vary in size and/or shape relative to each other. As another example, the liquid ports 46 may vary in size and/or shape relative to each other. One or more of the air ports 42 may vary in size and/or shape relative to one or more of the liquid ports 46. Alternatively, the air ports 42 and the liquid ports 46 may each have a common shape and/or size.

Figure 6:
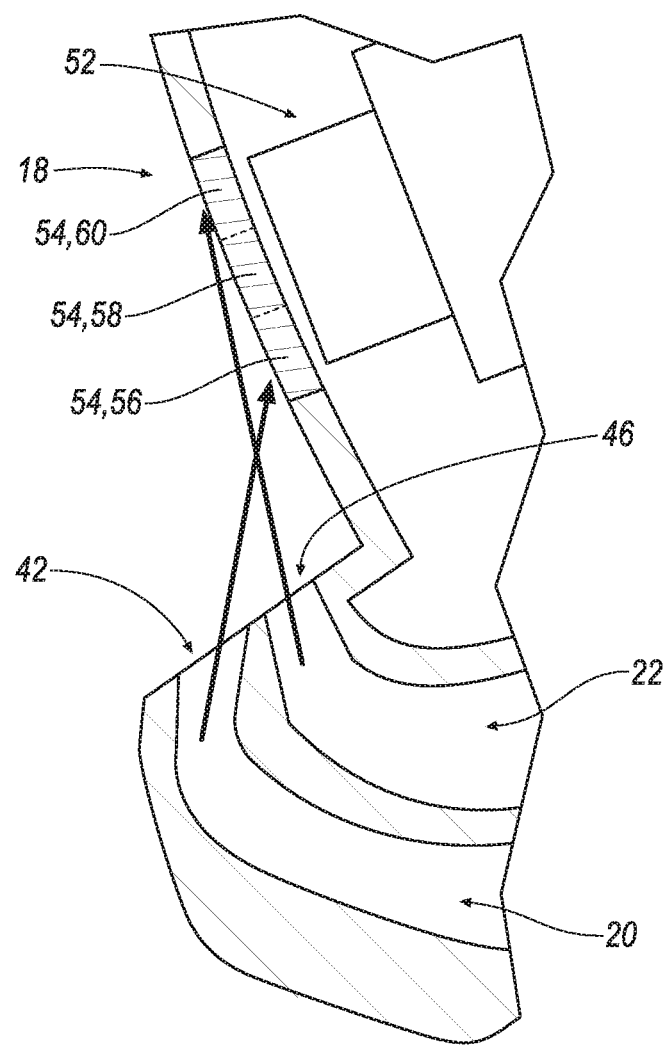
FIG. 6 is a cross-sectional view of a portion of the vehicle object-detection sensor assembly with the directions in which the air port and the liquid port are aimed are identified with arrows.

The air source 20 pressurizes air and the pressurized air exits the housing 26 through the air port 42 adjacent the sensor window 18. The liquid source 22 pressurizes liquid and the pressurized liquid exits the liquid source 22 through the liquid port 46 adjacent the sensor window 18. With reference to FIG. 6, the air port 42 and the liquid port 46 are aimed toward the sensor window 18 in intersecting directions (identified with arrows in FIG. 6). In other words, the pressurized air and pressurized liquid intersect in front of the sensor window 18. The air pressure of the air exiting the air port 42 and the liquid pressure of the liquid exiting the liquid port 46 may be adjusted to aim the liquid at the contaminant to remove the contaminant. The computer 10 described below applies the combination of air pressure settings for the air source 20 and liquid pressure settings for liquid source 22 to reach a desired zone 54 of the sensor window 18 and remove the contaminant in the zone 54.

As an example and as shown in FIG. 3, the sensor window 18 may be divided into three zones 54. The three zones 54 include a first zone 56 (which is closest to the air port 42 and the liquid port 46), a second zone 58, and a third zone 60 (which is farthest from the air port 42 and the liquid port 46).

Figure 7A:
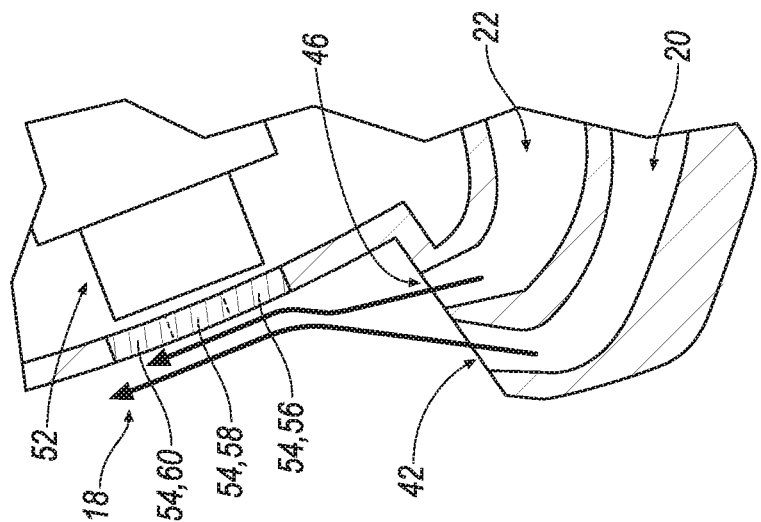
FIG. 7A shows the flow of air and liquid (identified with arrows) during a combination of a HIGH air pressure setting and a LOW liquid pressure setting.

To remove the contaminant in the first zone 56, as shown in FIG. 7A, the computer 10 applies the combination of the air pressure setting of HIGH and the liquid pressure setting of LOW to remove the contaminant in the first zone 56. The air pressure setting of HIGH has enough force to push and direct the liquid to the first zone 56.

Figure 7B:
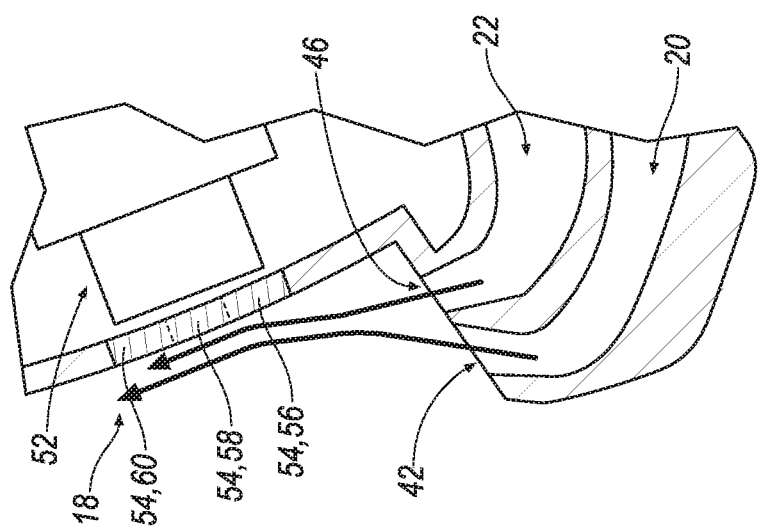
FIG. 7B shows the flow of air and liquid (identified with arrows) during a combination of a MEDIUM air pressure setting and a MEDIUM liquid pressure setting.

To remove the contaminant in the second zone 58, as shown in FIG. 7B, the computer 10 applies the combination of the air pressure setting of MEDIUM and the liquid pressure setting of MEDIUM to remove the contaminant in the second zone 58. The liquid exiting the liquid port 46 at the liquid pressure setting of MEDIUM is able to travel farther than the first zone 56 and the air exiting the air port 42 at the air pressure setting of MEDIUM has enough force to push and direct the liquid to the second zone 58.

Figure 7C:
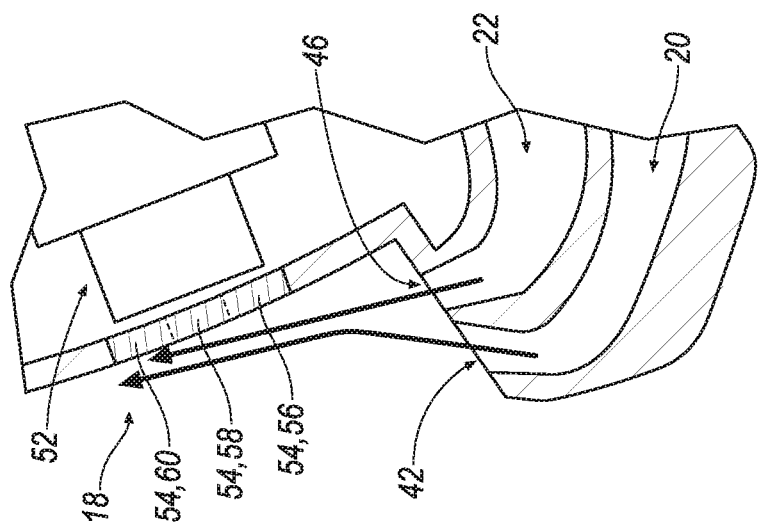
FIG. 7C shows the flow of air and liquid (identified with arrows) during a combination of a LOW air pressure setting and a HIGH liquid pressure setting.

To remove the contaminant in the third zone 60, as shown in FIG. 7C, the computer 10 applies the combination of the air pressure setting of LOW and the liquid pressure setting of HIGH to remove the contaminant in the third zone 60. The liquid pressure setting of HIGH may allow the liquid exiting the liquid port 46 have enough force to reach the third zone 60, and the air pressure setting of LOW may not have enough force to redirect the liquid but may have enough force to envelope the liquid and prevent the liquid from spreading. In other words, the air pressure setting of LOW may help concentrate the liquid on the third zone 60. While three zones 58 and three air pressure settings and liquid pressure settings are described in the example above, the sensor window 18 may be divided into any suitable number of zones 54, and the computer 10 may apply any suitable number of different air pressure settings and liquid pressure settings to direct the pressurized liquid to the desired zone 54.

The computer 10 applies a range of combinations of air pressure settings for the air source 20 and liquid pressure settings for liquid source 22 which eliminates the need to stop the pressurized air flowing across the sensor window 18 when the pressurized liquid is flowing across the sensor window 18. Accordingly, the air ports 42 may always create at least an air curtain across the sensor window 18, and may also direct the liquid exiting the liquid port 46.

The application of the range of combinations of air pressure settings for the air source 20 and liquid pressure settings for liquid source 22 on the sensor window 18 directs the pressurized air and the pressurized liquid to specifically clean a particular zone 54 of the sensor window 18 by preventing and controlling liquid droplets separation. This maximizes the volume of the pressurized liquid reaching the sensor window 18.

The computer 10 includes a processor 14 and a memory 16. The memory 16 stores processor-executable instructions. In other words, the processor 14 is programmed to execute the processor-executable instructions stored in the memory 16.

The processor 14 is programmed to receive data indicating the contaminant on the sensor window 18 of the vehicle 12, determine the combination of the air pressure setting of the air source 20 and the liquid pressure setting of the liquid source 22 to remove the contaminant from the sensor window 18, and set the air source 20 to the air pressure setting and the liquid source 22 to the liquid pressure setting.

As previously mentioned, the data indicates whether there is the contaminant on the sensor window 18. As an example, the data indicating there is the contaminant on the sensor window 18 may be generated by the object-detection sensor 52 adjacent the respective sensor window 18. The object-detection sensor 52 may indicate there is the contaminant on the sensor window 18 when the object-detection sensor 52 is unable to sense light passing through any one of the zones 54.

The data may include the location of the contaminant on the sensor window 18. The location of the contaminant on the sensor window 18 may be generated by the related object-detection sensor 52. The object-detection sensor 52 may identify the location of the contaminant on the sensor window 18 based on identifying the zones 54 through which the object-detection sensor 52 is unable to sense light.

The data may include the size of the contaminant on the sensor window 18. The size of the contaminant on the sensor window 18 may be generated by the related object-detection sensor 52. The object-detection sensor 52 may identify the size of the contaminant on the sensor window 18 based on identifying the zones 54 through which the object-detection sensor 52 is unable to sense light and the area covered by the affected zones 54.

As set forth above, the processor 14 is programmed to receive data that may indicate the contaminant on the sensor window 18. When the processor 14 receives data that indicates the contaminant on the sensor window 18, the processor 14 determines the combination of air pressure setting of the air source 20 and the liquid pressure setting of the liquid source 22 to remove the contaminant from the sensor window 18 based on various factors.

The various factors may include the location and the size of the contaminant on the sensor window 18. The processor 14 may receive data that includes the location of the contaminant on the sensor window 18, and the processor 14 may be programmed to determine the combination based at least on the location of the contaminant on the sensor window 18. The processor 14 may consider the distance from the air port 42 to the location of the contaminant as well as the distance from the liquid port 46 to the location of the contaminant when the processor 14 determines the combination of air pressure setting and liquid pressure setting. As an example and as previously mentioned, when the location of the contaminant is relatively close to the air port 42 and the liquid port 46, the processor 14 may select the combination of the air pressure setting of HIGH and the liquid pressure setting of LOW to remove the contaminant. Also as another example and as previously mentioned, when the location of the contaminant is relatively far from the air port 42 and the liquid port 46, the processor 14 may select as the combination an air pressure of LOW and a liquid pressure setting of HIGH to reach and remove the contaminant.

The processor 14 may receive data that includes the size of the contaminant on the sensor window 18, and the processor 14 may be programmed to determine the combination based at least on the size of the contaminant on the sensor window 18. The size of the contaminant can range from a small size contained within one zone to a large size covering multiple zones 54. When the size of the contaminant is small, the processor 14 may select as the combination the air pressure setting of LOW and the liquid pressure setting of LOW to remove the contaminant. Alternatively, if the size of the contaminant is large, covering multiple zones 54, the processor 14 may select as the combination the air pressure setting of HIGH and the liquid pressure setting of HIGH to break and remove the contaminant.

In addition to or as an alternative to receiving and determining the combination based on the location and the size of the contaminant, the processor 14 may receive data indicating a speed of the vehicle 12 and may determine the combination based on at least the speed of the vehicle 12. Where the vehicle 12 is in motion, the processor 14 may consider the pressure exerted on the sensor window 18 based on the speed of the vehicle 12 and the processor 14 may determine the combination where the air source 20 exerts less air pressure and the liquid source 22 exerts less liquid pressure, e.g. the air pressure setting may be LOW and the liquid pressure setting may be LOW. Alternatively, when the vehicle 12 is stationary, the processor 14 may determine the combination where the air pressure setting is MEDIUM or HIGH and the liquid pressure setting is also MEDIUM or HIGH.

The processor 14 may receive data indicating the direction of movement of the vehicle 12 and may determine the combination based on at least the direction of movement of the vehicle 12. The processor 14 may consider the direction of movement of the vehicle 12 in relation to direction the sensor window 18 is facing. As an example, if the sensor window 18 is forward facing and the vehicle 12 is moving in a forward direction, the processor 14 may consider external air pressure exerted on the sensor window 18 as the sensor window 18 faces forward when the vehicle 12 is moving forward. In such a case, the processor 14 may determine the combination where the air source 20 exerts less air pressure and the liquid source 22 exerts less liquid pressure, e.g. the air pressure setting may be LOW and the liquid pressure setting may be LOW. Alternatively, when the vehicle 12 is moving backwards and the sensor window 18 is facing the transverse direction, the processor 14 may consider external air pressure exerted on the air ports 42 and liquid ports 46 facing the backward direction and the processor 14 may determine the combination where the air pressure setting is HIGH and the liquid pressure setting is also HIGH to counteract the opposing external air pressure exerted on the air port 42 and liquid port 46 from the direction of movement of the vehicle 12.

The processor 14 may consider the speed of the vehicle 12 and the direction of the vehicle 12 together to determine the combination. The processor 14 may use an algorithm to calculate the combination of the air pressure setting and the liquid pressure setting to remove the contaminant. Alternatively and/or additionally, the processor 14 may use a look up table to compute the combination of the air pressure setting and the liquid pressure setting to remove the contaminant. The processor 14 may use one or more of the location and the size of the contaminant, the speed of the vehicle 12 and the direction of movement of the vehicle 12. The processor 14 may use any factors that may be suitable in determining the combination of the air pressure setting and the liquid pressure setting to remove the contaminant.

The processor 14 may determine more than one combination of the air pressure setting and the liquid pressure setting. In other words, the processor 14 may determine a series of combinations that may include the combination of the air pressure setting and the liquid pressure setting, and a second combination of a second air pressure setting and a second liquid pressure setting. The second air pressure setting may be lower than the air pressure setting and the second liquid pressure setting may be lower than the liquid pressure setting.

Upon determining the combination, the processor 14 is programmed to set the air source 20 to the air pressure setting based on the combination and to set the liquid source 22 to the liquid pressure setting also based on the combination.

Where the processor 14 determines the series of combinations, the processor 14 is initially programmed to set the air source 20 to the air pressure setting based on the combination and to set the liquid source 22 to the liquid pressure setting based on the combination. The processor 14 may wait for a prescribed time period before setting the air source 20 to the second air pressure setting based on the second combination and setting the liquid source 22 to the second liquid pressure setting based on the second combination.

The processor 14 may activate and deactivate the air source 20 and the liquid source 22 in various time-based sequences. The time-based sequences include but are not limited to a static configuration, a two-step configuration and a pulse configuration.

Figure 9:
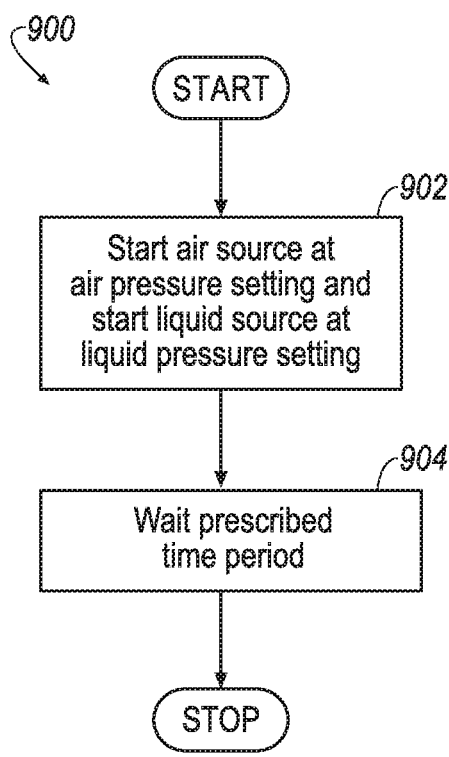
FIG. 9 is a flowchart of an example process for a static configuration.

In the static configuration and as shown in FIG. 9, the processor 14 sets the air source 20 to the air pressure setting and sets the liquid source 22 to the liquid pressure setting. The processor 14 activates the air source 20 and the liquid source 22, waits for the prescribed time period to expire, after which the processor 14 receives feedback information on whether there is still the contaminant on the sensor window 18. If the processor 14 receives data indicating no contaminant on the sensor window 18, the processor 14 may set the air source 20 to a lower air pressure setting and/or the liquid source 22 to a lower liquid pressure setting. More specifically, the processor 14 may deactivate the air source 20 and/or the liquid source 22. If the processor 14 receives data indicating the contaminant remains on the sensor window 18, the processor 14 may initiate a new process, starting with determining the combination.

Figure 10:
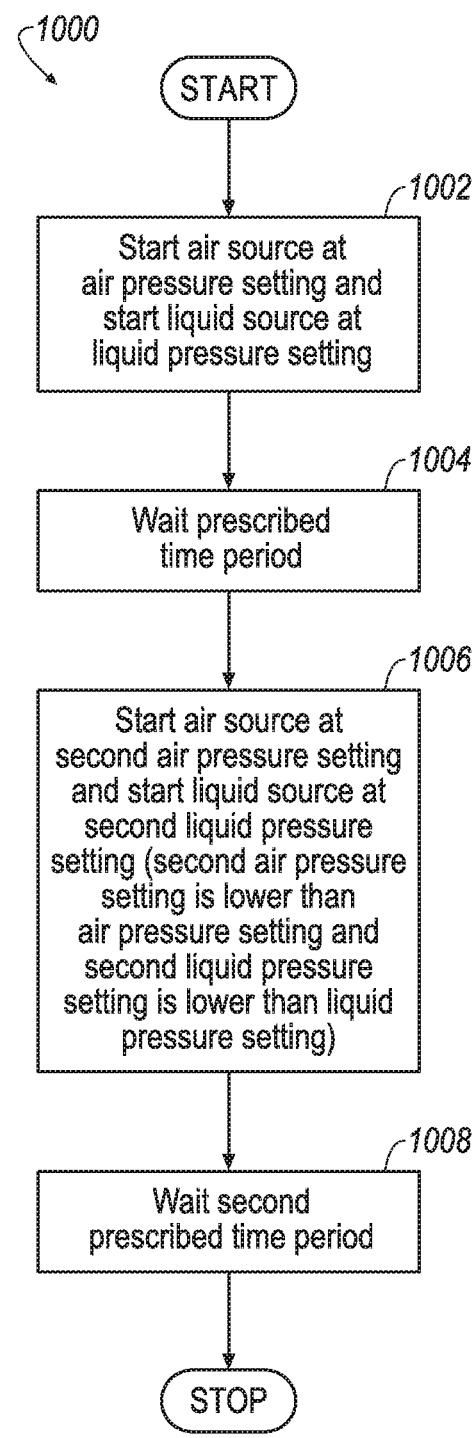
FIG. 10 is a flowchart of an example process for a two-step configuration.

In the two-step configuration and as shown in FIG. 10, the processor 14 sets the air source 20 to the air pressure setting and sets the liquid source 22 to the liquid pressure setting. The processor 14 activates the air source 20 and the liquid source 22, waits for the prescribed time period to expire, after which the processor 14 sets the air source 20 to the second air pressure setting and sets the liquid source 22 to the second liquid pressure setting. In one example, the second air pressure setting is lower than the air pressure setting and the second liquid pressure setting is lower than the liquid pressure setting. The processor 14 waits for a second prescribed time period. The second prescribed time period may be the same as the prescribed time period. Alternatively, the second prescribed time period may be different from the prescribed time period. When the second prescribed time period expires, the processor 14 receives feedback information on whether there is still the contaminant on the sensor window 18. If the processor 14 receives data indicating no contaminant on the sensor window 18, the processor 14 may set the air source 20 to a lower air pressure setting and/or the liquid source 22 to a lower liquid pressure setting. More specifically, the processor 14 may deactivate the air source 20 and/or the liquid source 22. If the processor 14 receives data indicating the contaminant remains on the sensor window 18, the processor 14 may initiate a new process, starting with determining the combination.

Figure 11:
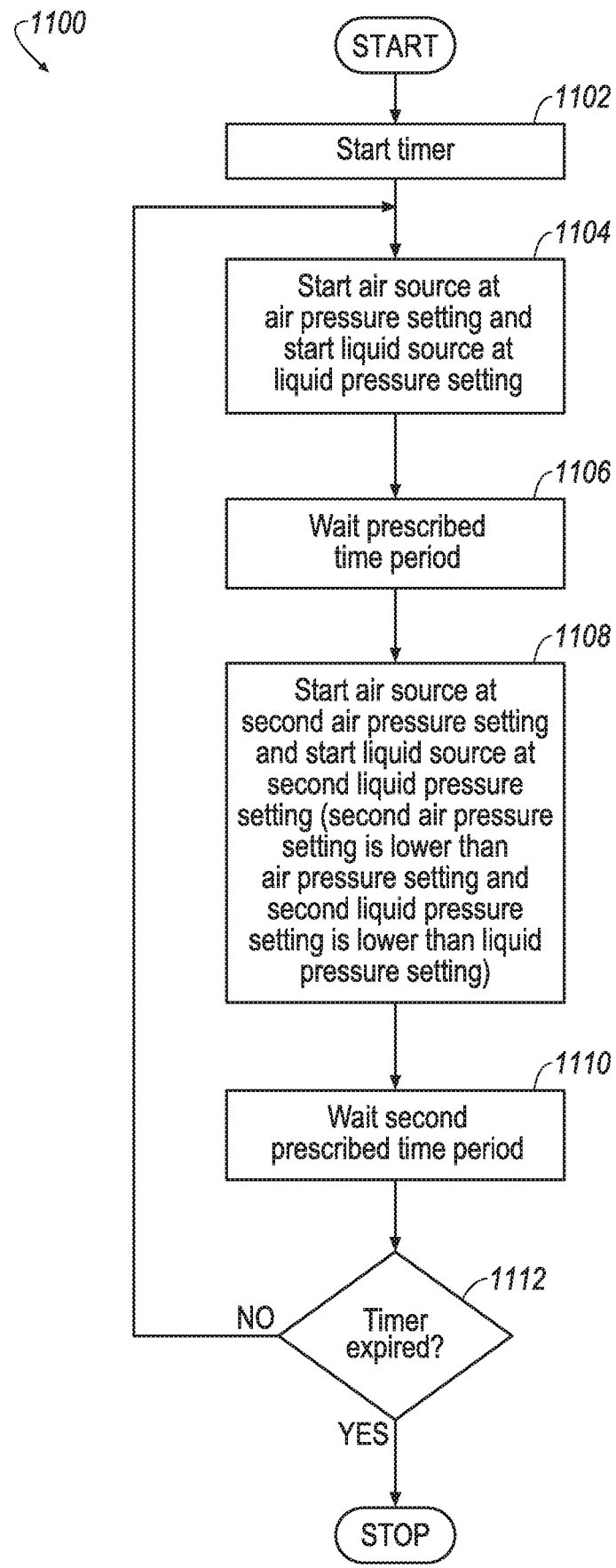
FIG. 11 is a flowchart of an example process for a pulse configuration.
Figure 12:
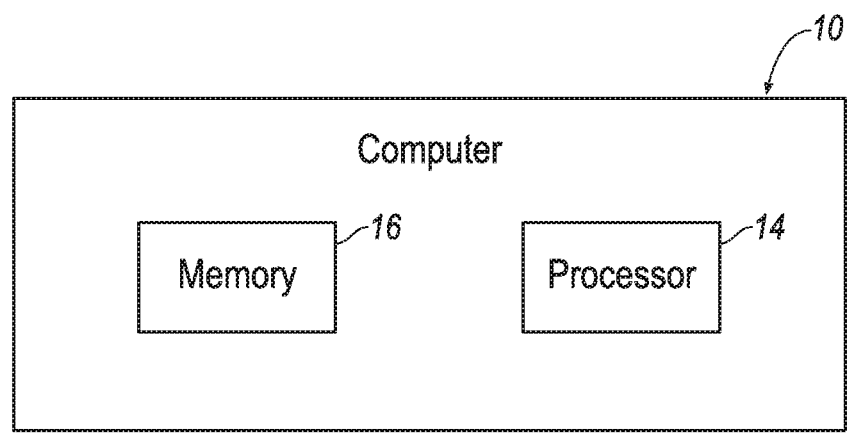
FIG. 12 is the example computer for determining the combination of the air pressure setting for the air source and the liquid pressure setting for a liquid source.

In the pulse configuration and as shown in FIG. 11, the processor 14 sets a timer (not shown) to a third prescribed time period and activates the timer. In this configuration, the processor uses the prescribed time period and the second prescribed time period. The third prescribed time period is longer than the sum of the prescribed time period and second prescribed time period. The processor 14 starts a process by setting the air source 20 to the air pressure setting and setting the liquid source 22 to the liquid pressure setting. The processor 14 activates the air source 20 and the liquid source 22, waits for the prescribed time period to expire, after which the processor 14 sets the air source 20 to the second air pressure setting and sets the liquid source 22 to the second liquid pressure setting. In one example, the second air pressure setting is lower than the air pressure setting and the second liquid pressure setting is lower than the liquid pressure setting. The processor 14 waits for the second prescribed time period after which the processor 14 checks if the timer with the third prescribed time period has expired. If the timer has not expired, the processor 14 returns to the start of the process and resets the air source 20 to the air pressure setting and the liquid source 22 to the liquid pressure setting and repeats the process until the timer expires. When the timer expires, the processor 14 receives feedback information on whether there is still the contaminant on the sensor window 18. If the processor 14 receives data indicating no contaminant on the sensor window 18, the processor 14 may set the air source 20 to a lower air pressure setting and/or the liquid source 22 to a lower liquid pressure setting. More specifically, the processor 14 may deactivate the air source 20 and/or the liquid source 22. If the processor 14 receives data indicating the contaminant remains on the sensor window 18, the processor 14 may initiate a new process, starting with determining the combination.

Figure 8:
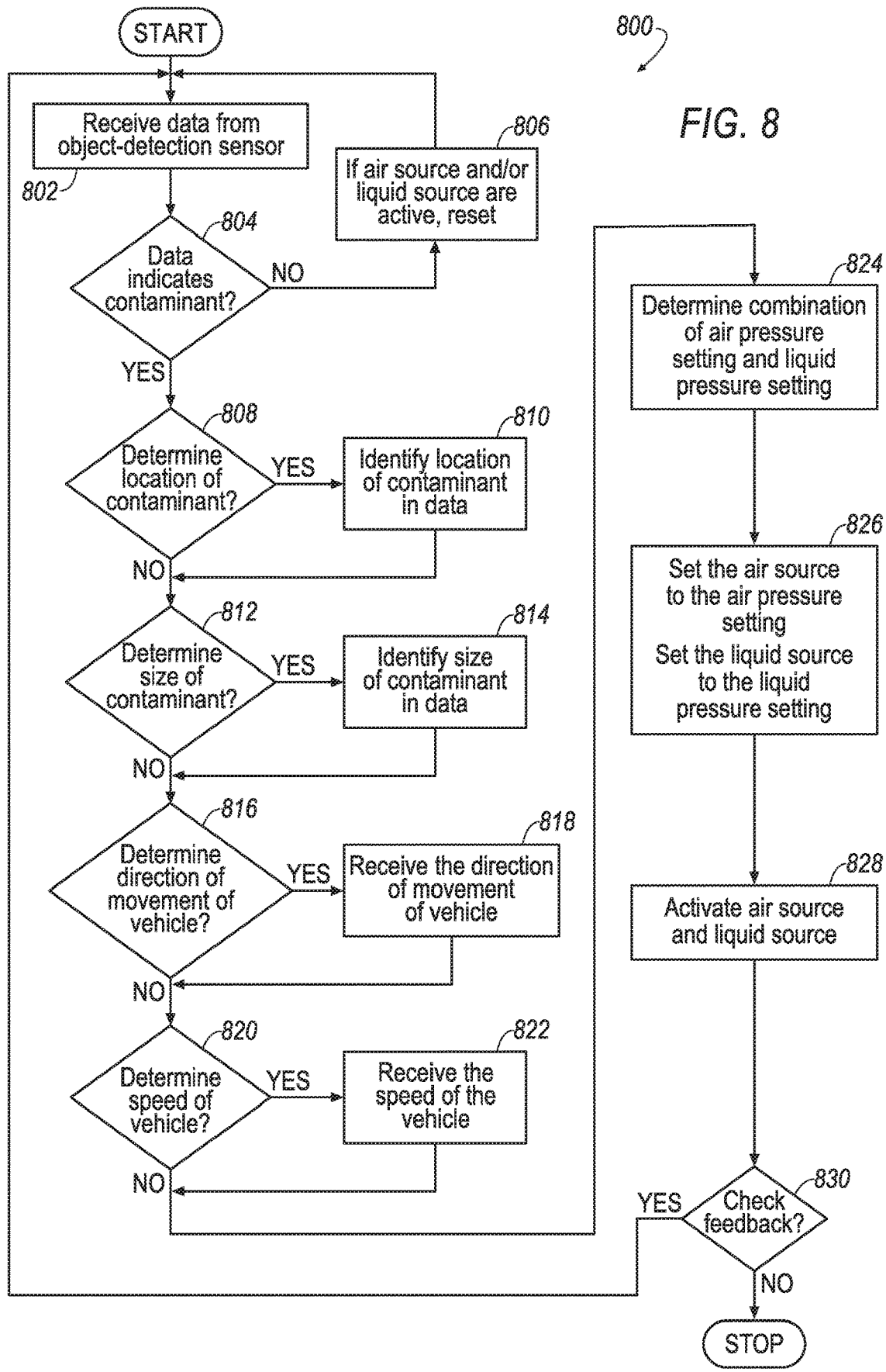
FIG. 8 is a flow chart for a process carried out by an example computer for determining the combination of the air pressure setting for the air source and the liquid pressure setting for a liquid source.

FIG. 8 is a flowchart of an example process 800 that may be implemented by the processor 14 to determine the combination of the air pressure setting of the air source 20 and the liquid pressure setting of the liquid source 22 to remove the contaminant from the sensor window 18, and to set the air source 20 to the air pressure setting and the liquid source 22 to the liquid pressure setting.

At block 802, the processor 14 receives data from the object-detection sensor 52 that identifies whether there is the contaminant on the sensor window 18. The data may also include information about the location and the size of the contaminant on the sensor window 18. The processor 14 proceeds to block 804.

At decision block 804, the processor 14 assesses whether the data received in block 802 indicates that there is the contaminant on the sensor window 18. If the data indicates that there is no contaminant on the sensor window 18, the processor 14 proceeds to block 806. If the data indicates that there is the contaminant, the processor 14 may proceed to block 808.

At block 806, the processor 14 resets the air source 20 and the liquid source 22 if the air source 20 and the liquid source 22 are currently active, and the processor returns to block 802 so that the processor 14 may receive data from the object-detection sensor that identifies whether there is the contaminant.

From blocks 808 to 822, the processor 14 reads in information that it needs to determine the combination of the air pressure setting and the liquid pressure setting.

At decision block 808, the processor 14 assesses whether the processor 14 requires the location of the contaminant to determine the combination of the air pressure setting and the liquid pressure setting. If the processor 14 concludes that the processor 14 requires the location of the contaminant to determine the combination, the processor 14 may proceed to block 810. If the processor 14 concludes that the processor 14 does not require the location of the contaminant, the processor 14 may proceed to block 812.

At block 810, the processor 14 identifies the location information within the data and retrieves the location information. The processor 14 proceeds to block 812.

At decision block 812, the processor 14 assesses if the processor 14 requires the size of the contaminant to determine the combination of the air pressure setting and the liquid pressure setting. If the processor 14 concludes that the processor 14 requires the size of the contaminant to determine the combination, the processor 14 may proceed to block 814. If the processor 14 determines that the processor 14 does not require the size of the contaminant, the processor 14 may proceed to block 816.

At block 814, the processor 14 identifies the size information within the data and retrieves the size information. The processor 14 proceeds to block 816.

At decision block 816, the processor 14 determines if the processor 14 requires direction of movement of the vehicle 12 to determine the combination of the air pressure setting and the liquid pressure setting. If the processor 14 determines that the processor 14 requires the direction of movement of the vehicle 12 to determine the combination, the processor may proceed to block 818. If the processor 14 determines that the processor 14 does not require the direction of the movement of the vehicle 12, the processor may proceed to block 820.

At block 818, the processor 14 receives information of the direction of movement of the vehicle 12. The processor 14 proceeds to block 820.

At decision block 820, the processor 14 determines if the processor 14 requires the speed of the vehicle 12 to determine the combination of air pressure setting and liquid pressure setting. If the processor 14 determines that the processor 14 requires the speed of the vehicle 12 to determine the combination, the processor may proceed to block 822. If the processor 14 determines that the processor 14 does not require the speed of the vehicle 12, the processor may proceed to block 824.

At block 822, the processor 14 receives information of the speed of the vehicle 12. The processor 14 proceeds to block 824.

At block 824, the processor 14 determines the combination of the air pressure setting and the liquid pressure setting required to release the contaminant. The processor 14 may output a single combination of the air pressure setting and the liquid pressure setting. Alternatively, the processor 14 may output the series of combinations of the air pressure settings and the liquid pressure settings. As an example, the series of combinations of the air pressure settings and the liquid pressure settings may include the combination of the air pressure setting and the liquid pressure setting and the second combination of the second air pressure setting and the second liquid pressure setting. The processor 14 may set the air source 20 and the liquid source 22 sequentially to the series of combinations of the air pressure settings and the liquid pressure settings respectively. The processor 14 proceeds to block 826.

At block 826, the processor 14 sets the air source 20 to the air pressure setting and the liquid source 22 to the liquid pressure setting. The processor 14 proceeds to 828.

At block 828, the processor 14 activates the air source 20 and the liquid source 22. As an example, in block 828, the processor 14 can execute one of three configurations. The three configurations are the static configuration, the two-step configuration and the pulse configuration. After executing one of the three configurations, the processor 14 proceeds to block 830.

At the decision block 830, the processor 14 determines whether the feedback verification option has been selected. If the feedback verification option has not been selected, the processor 14 turns off the air source 20 and the liquid source 22. If the feedback verification option has been selected, the air source 20 and the liquid source 22 may remain on and the processor 14 returns to block 802.

As illustrated in FIG. 9, the processor 14 activates the air source 20 and the liquid source 22 in the static configuration. In other words, FIG. 9 is a flowchart of an example process 900 that may be implemented by the processor 14 to activate the air source 20 and the liquid source 22 in the static configuration.

At block 902, the processor 14 starts up the air source 20 at the air pressure setting and liquid source 22 at the liquid pressure setting based on the combination of the air pressure setting and the liquid pressure setting. The processor 14 proceeds to block 904.

At block 904, the air source 20 continues to run at the air pressure setting and the liquid source 22 continues to run at the liquid pressure setting while the processor 14 waits for the prescribed time period to expire. When the prescribed time period expires, the processor 14 proceeds to block 830 in FIG. 8.

As illustrated in FIG. 10, the processor 14 activates the air source 20 and the liquid source 22 in the two-step configuration. In other words, FIG. 10 is a flowchart of an example process 1000 that may be implemented by the processor 14 to activate the air source 20 and the liquid source 22 in the two-step configuration.

The two-step configuration may use the series of combinations of the air pressure settings and the liquid pressure settings. Specifically, the series of combinations of the air pressure setting and the liquid pressure setting includes the combination of the air pressure setting and the liquid pressure setting, and the second combination of the second air pressure setting and the second liquid pressure setting.

At block 1002, the processor 14 starts up the air source 20 at the air pressure setting and liquid source 22 at the liquid pressure setting based on the combination of the air pressure setting and the liquid pressure setting. The processor 14 proceeds to block 1004.

At block 1004, the air source 20 continues to run at the air pressure setting and the liquid source 22 continues to run at the liquid pressure setting while the processor 14 waits for the prescribed time period to expire. When the prescribed time period expires, the processor 14 proceeds to block 1006.

At block 1006, the processor 14 starts up the air source 20 at the second air pressure setting and the liquid source 22 at the second liquid pressure setting based on the second combination of the second air pressure setting and the second liquid pressure setting. The processor 14 proceeds to block 1008.

At block 1008, the air source 20 and the liquid source 22 continue to run at the second air pressure setting and the second liquid pressure setting respectively while the processor 14 waits for the second prescribed time period. When the second prescribed time period expires, the processor 14 proceeds to block 830, shown in FIG. 8.

As illustrated in FIG. 11, the processor 14 activates the air source 20 and the liquid source 22 in the pulse configuration. In other words, FIG. 11 is a flowchart of an example process 1100 that may be implemented by the processor 14 to activate the air source 20 and the liquid source 22 in the pulse configuration.

The pulse configuration may use the series of combinations of the air pressure settings and the liquid pressure settings. As previously mentioned, the series of combinations of the air pressure settings and the liquid pressure settings includes the combination of the air pressure setting and the liquid pressure setting, and the second combination of the second air pressure setting and the second liquid pressure setting. As previously mentioned, the second air pressure setting may be lower than the air pressure setting and the second liquid pressure setting may be lower than the liquid pressure setting.

The pulse configuration also uses the prescribed time period, the second prescribed time period and the third prescribed time period. The second prescribed time period may be the same as the prescribed time period. Alternatively, the second prescribed time period may be different from the prescribed time period.

At block 1102, the processor 14 starts the timer set to the third prescribed time period. The processor 14 proceeds to block 1104.

At block 1104, the processor 14 starts up the air source 20 at the air pressure setting and liquid source 22 at liquid pressure setting based on the combination of the air pressure setting and the liquid pressure setting. The processor 14 proceeds to block 1106.

At block 1106, the air source 20 and the liquid source 22 continue to run at the air pressure setting and the liquid pressure setting respectively while the processor 14 waits for the prescribed time period. When the prescribed time period expires, the processor 14 proceeds to block 1108.

At block 1108, the processor 14 starts up the air source 20 at the second air pressure setting and liquid source 22 at the second liquid pressure setting based on the second combination of the second air pressure setting and the second liquid pressure setting.

At block 1110, the air source 20 and the liquid source 22 continue to run at the second air pressure setting and the second liquid pressure setting respectively while the processor 14 waits for the second prescribed time period. When the second prescribed time period expires, the processor 14 proceeds to block 1112.

At block 1112, the processor 14 checks whether the timer set to the third prescribed time period has expired. If the third prescribed time period has not expired, the processor 14 returns to block 1104. If the third prescribed time period has expired, the processor 14 proceeds to block 830, in FIG. 8.

In general, the computing systems and/or devices described may employ any of a number of computer operating systems, including, but by no means limited to, versions and/or varieties of the Microsoft Automotive® operating system, the Microsoft Windows® operating system, the Unix operating system (e.g., the Solaris® operating system distributed by Oracle Corporation of Redwood Shores, Calif.), the AIX UNIX operating system distributed by International Business Machines of Armonk, N.Y., the Linux operating system, the Mac OSX and iOS operating systems distributed by Apple Inc. of Cupertino, Calif., the BlackBerry OS distributed by Blackberry, Ltd. of Waterloo, Canada, and the Android operating system developed by Google, Inc. Examples of computing devices (not shown) include, without limitation, an on-board vehicle computer, a computer workstation, a server, a desktop, notebook, laptop, or handheld computer, or some other computing system and/or device.

Computing devices generally include computer-executable instructions, where the instructions may be executable by one or more computing devices such as those listed above. Computer-executable instructions may be compiled or interpreted from computer programs created using a variety of programming languages and/or technologies, including, without limitation, and either alone or in combination, Java™, C, C++, Visual Basic, Java Script, Perl, etc. Some of these applications may be compiled and executed on a virtual machine, such as the Java Virtual Machine, the Dalvik virtual machine, or the like. In general, a processor 14 (e.g., a microprocessor) receives instructions, e.g., from a memory 16, a computer-readable medium, etc., and executes these instructions, thereby performing one or more processes, including one or more of the processes described herein. Such instructions and other data may be stored and transmitted using a variety of computer-readable media.

A computer-readable medium (also referred to as a processor-readable medium) includes any non-transitory (e.g., tangible) medium that participates in providing instructions that may be read by a computer (e.g., by a processor of a computer). Such a medium may take many forms, including, but not limited to, non-volatile media and volatile media. Non-volatile media may include, for example, optical or magnetic disks and other persistent memory 16. Volatile media may include, for example, dynamic random access memory (DRAM), which typically constitutes a main memory. Such instructions may be transmitted by one or more transmission media, including coaxial cables, copper wire and fiber optics, including the wires that comprise a system bus coupled to a processor 14 of a computer. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

Databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store is generally included within a computing device employing a computer operating system such as one of those mentioned above, and are accessed via a network in any one or more of a variety of manners. A file system may be accessible from a computer operating system, and may include files stored in various formats. An RDBMS generally employs the Structured Query Language (SQL) in addition to a language for creating, storing, editing, and executing stored procedures, such as the PL/SQL language mentioned above.

In some examples, system elements may be implemented as computer-readable instructions (e.g., software) on one or more computing devices (e.g., servers, personal computers, etc.), stored on computer readable media associated therewith (e.g., disks, memories, etc.). A computer program product may comprise such instructions stored on computer readable media for carrying out the functions described herein.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

The disclosure has been described in an illustrative manner, and it is to be understood that the terminology which has been used is intended to be in the nature of words of description rather than of limitation. Many modifications and variations of the present disclosure are possible in light of the above teachings, and the disclosure may be practiced otherwise than as specifically described.

What is claimed is:

1. A computer comprising a processor and a memory storing processor-executable instructions, the processor programmed to:
   receive data indicating a contaminant on a sensor window of a vehicle;
   determine a combination of an air pressure setting of an air source and a liquid pressure setting of a liquid source to remove the contaminant from the sensor window; and
   set the air source to the air pressure setting and the liquid source to the liquid pressure setting;
   wherein the sensor window has zones and the data includes a location of the contaminant on one or more zones of the sensor window, and the processor is further programmed to determine the combination based at least on the location of the contaminant on the sensor window on the one or more zones to concentrate pressurized liquid from the liquid source on the one or more zones on which a contaminant is located; and
   simultaneously operate the air source at the air pressure setting and the liquid source at the liquid pressure setting.

2. The computer of claim 1, wherein the data includes a size of the contaminant on the sensor window, and the processor is further programmed to determine the combination based at least on the size of the contaminant on the sensor window.

3. The computer of claim 1, wherein the processor is further programmed to receive data indicating a speed of the vehicle and to determine the combination based at least on the speed of the vehicle.

4. The computer of claim 1, wherein the processor is further programmed to receive data indicating the direction of movement of the vehicle and to determine the combination based at least on the direction of movement of the vehicle.

5. The computer of claim 4, wherein the processor is further programmed to receive data indicating a speed of the vehicle and to determine the combination based at least on the speed of the vehicle.

6. The computer of claim 1, wherein the processor is further programmed to set at least one of the air source to a second air pressure setting and the liquid source to a second liquid pressure setting, after a prescribed time period, wherein the second air pressure setting is lower than the air pressure setting and the second liquid pressure setting is lower than the liquid pressure setting to maintain an air curtain across the sensor window when not operating to remove a contaminant from the sensor window.

7. The computer of claim 1, wherein the processor is further programmed to set the air source to a second air pressure setting after a prescribed time period, and the processor is programmed to reset the air source to the air pressure setting after a second prescribed time period, wherein the second air pressure setting is lower than the air pressure setting to maintain an air curtain across the sensor window when not operating to remove a contaminant from the sensor window.

8. The computer of claim 1, wherein the processor is further programmed to set the liquid source to a second liquid pressure setting after a prescribed time period, and the processor is programmed to reset the liquid source to the liquid pressure setting after a second prescribed time period, wherein the second liquid pressure setting is lower than the liquid pressure setting.

9. The computer of claim 1, wherein the processor is further programmed to set at least one of the air source to a lower air pressure setting and the liquid source to a lower liquid pressure setting in response to the data indicating no contaminant on the sensor window to maintain an air curtain across the sensor window when not operating to remove a contaminant from the sensor window.

10. A method executable by a processor in a computer comprising:
    receiving data indicating a contaminant on a sensor window;
    determining a combination of an air pressure setting of an air source and a liquid pressure setting of a liquid source to remove the contaminant from the sensor window; and
    setting the air source to the air pressure setting and the liquid source to the liquid pressure setting;
    determining the combination based at least on the location of the contaminant on one or more zones of the sensor window to concentrate pressurized liquid from the liquid source to the one or more zones on which a contaminant is located; and
    simultaneously operating the air source at the air pressure setting and the liquid source at the liquid pressure setting.

11. The method of claim 10, wherein the data includes a size of the contaminant on the sensor window, and further comprising determining the combination based at least on the size of the contaminant on the sensor window.

12. The method of claim 10, further comprising receiving data indicating a speed of the vehicle and determining the combination based at least on the speed of the vehicle.

13. The method of claim 10, further comprising receiving data indicating the direction of movement of the vehicle and determining the combination based at least on the direction of the movement of the vehicle.

14. The method of claim 13, further comprising receiving data indicating a speed of the vehicle and determining the combination based at least on the speed of the vehicle.

15. The method of claim 10, further comprising:
    setting at least one of the air source to a second air pressure setting and the liquid source to a second liquid pressure setting, after a prescribed time period, wherein the second air pressure setting is lower than the air pressure setting and the second liquid pressure setting is lower than the liquid pressure setting and maintaining an air curtain across the sensor window when not operating to remove a contaminant from the sensor window.

16. The method of claim 10, further comprising:
    setting the air source to a second air pressure setting after a prescribed time period; and
    resetting the air source to the air pressure setting after a second prescribed time period, wherein the second air pressure setting is lower than the air pressure setting and maintaining an air curtain across the sensor window when not operating to remove a contaminant from the sensor window.

17. The method of claim 10, further comprising:
setting the liquid source to a second liquid pressure setting after a prescribed time period; and
resetting the liquid source to the liquid pressure setting after a second prescribed time period, wherein the second liquid pressure setting is lower than the liquid pressure setting.

18. The method of claim 10, further comprising:
setting at least one of the air source to a lower air pressure setting and the liquid source to a lower liquid pressure setting in response to the data indicating no contaminant on the sensor window and maintaining an air curtain across the sensor window when not operating to remove a contaminant from the sensor window.

* * * * *